US008512737B1

(12) United States Patent
Consigny et al.

(10) Patent No.: US 8,512,737 B1
(45) Date of Patent: Aug. 20, 2013

(54) EMBOLIC DELIVERY OF THERAPEUTIC AGENTS

(75) Inventors: Paul Consigny, San Jose, CA (US); Thierry Glauser, Redwood City, CA (US); John Stankus, Campbell, CA (US); Stephen Pacetti, San Jose, CA (US); Santosh Prabhu, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 992 days.

(21) Appl. No.: 12/132,570

(22) Filed: Jun. 3, 2008

(51) Int. Cl.
*A61K 9/0024* (2006.01)
*A61K 9/1647* (2006.01)
*A61K 27/54* (2006.01)
*A61K 27/18* (2006.01)
*A61K 27/58* (2006.01)
*A61K 35/34* (2006.01)
*A61K 38/00* (2006.01)
*A61K 35/44* (2006.01)

(52) U.S. Cl.
USPC ............................................. 424/426; 424/569

(58) Field of Classification Search
None
See application file for complete search history.

(56) References Cited

U.S. PATENT DOCUMENTS

| | | | |
|---|---|---|---|
| 2005/0123614 A1* | 6/2005 | Kim et al. | 424/489 |
| 2005/0186261 A1* | 8/2005 | Avelar et al. | 424/445 |
| 2006/0034925 A1* | 2/2006 | Au et al. | 424/468 |
| 2006/0189520 A1* | 8/2006 | Brand et al. | 514/12 |
| 2007/0184082 A1* | 8/2007 | Magdassi et al. | 424/422 |
| 2007/0207211 A1* | 9/2007 | Zeigerson | 424/489 |
| 2008/0039362 A1* | 2/2008 | Shebuski et al. | 514/2 |

FOREIGN PATENT DOCUMENTS

WO    WO 2005/079703    9/2005

OTHER PUBLICATIONS

Hu et al. "Nanoparticle Engineering Process for Enhancing the Dissolution Rates of Poorly Water Soluble Drugs". Drug Development and Industrial Pharmacy vol. 30, No. 3, pp. 233-245 2004.*
Giovanna et al. "Nanostructured Microspheres Produced by Supercritical Fluid Extraction of Emulsions" Biotechnology and Bioenineering vol. 10o, No. 5, Aug. 1, 2008. (Article Published Feb. 27, 2008).*
Hua et al. "Experimental and Numerical Studies of Droplet and Formation in Electrohydrodynamic Atomiation", Abstract 1 pg. (2008).*
"Determination of Halofuginone Hydrobromide in Medical Animal Feeds", Analytical Methods Committee, Analyst. vol. 108, pp. 1252-1256 (1983).
"Galenic principles of modern skin care products", Skin Care Forum, Issue 25, downloaded from www.scf-online.com/english/25_e/galenic Feb. 5, 2008, 16 pgs.
"supercritical fluid", Sci-Tech. Dictionary, downloaded from www.answers.com/topic/supercritical-fluid?cat=technology, Feb. 5, 2008, 3 pgs.
Berkland et al., "Fabrication of PLG microspheres with precisely controlled and monodisperse size distributions", J. of Controlled Release 73 pp. 59-74 (2001).
Bonegio et al., "Rapamycin Ameliorates Proteinuria-Associated Tubulointerstitial Inflammation and Fibrosis in Experimental Membranous Nephropathy", J. of Am. Soc. of Nephrology, 16, pp. 2063-2072 (2005).
Cao et al, "Inhibition of Mammalian Target of Rapamycin or Apoptotic Pathway induces Autphagy and Radiosensitizes PTEN Null Prostate Cancer Cells", Cancer Res 66, pp. 10040-10047 (2006).
Daniel et al., "Proinflammatory Effects in Experimental Mesangial Proliferative Glomerulonephritis of the Immunosuppressive Agent SDZ RAD, a Rapamycin Derivative", Exp. Nephrol 8, pp. 52-62 (2000).
DiJoseph et al., "The Effect of Rapamycin on Kidney Function in the Sprague-Dawley Rat", Transplantation vol. 53, No. 3 pp. 507-513 (1992).
Freitas, "Arteriovenous Microcirculation", Nanomedicine, vol. 1: Basic Capabilities, 4 pgs. (2003).
Gasparini et al., "Membrane Emulsification for Polyd, L-Lactide-Co-Glycolide Acid Microparticle Production: Influencing Factors", Abstract, Particle Formation and Crystallization Processess from Liquids, Slurries and Emulsions, the Preliminary program for 2007 Annual Meeting.
Guertin' et al., "An expanding role for mTOR in cancer", Trends in Molecular Medicine vol. 11, No. 8, 353-361 (2005).
Hua et al., "Experimental and Numerical Studies of Droplet and Particle Formation in Electrohydrodynamic Atomization", Abstract, 1 pg. (2008).
Ishida et al., "A combinatorial approach to producing sterically stabilized (Stealth) immunoliposomal drugs", FEBS Letters 460, pp. 129-133 (1999).
Jian-Kang Chen et al., "Role of Mammalian Target of Rapamycin Signaling in Compensatory Renal Hypertrophy", J. of Am. Soc. of Nephrology, 16, pp. 1384-1391 (2005).
Kuang et al., "On the Fabrication of Microparticles Using Electrohydrodynamic Atomization Method", Molecular Engineering of Biological and Chemical Systems (MEBCS), 5 pgs. (2005).
Lloberas et al., "Mammalian Target of Rapamycin Pathway Blockade Slows Progression of Diabetic Kidney Disease in Rats", J. of Am. Soc. of Nephrology, 17, pp. 1395-1404 (2006).
Membrane Emulsification, Introduction, downloaded from www.chemsoc.org/ExemplarChem/entries2004/loughborough_cheng+woo/cheng+ Mar. 28, 2008, 1 pg.

(Continued)

*Primary Examiner* — Robert A Wax
*Assistant Examiner* — Danah Al-Awadi
(74) *Attorney, Agent, or Firm* — Squire Sanders (US) LLP

(57) ABSTRACT

This application is directed to means for embolic delivery of therapeutic agents to an afflicted organ in the body of a patient.

29 Claims, No Drawings

(56) References Cited

OTHER PUBLICATIONS

Panchapakesan et al., "Drug Insight: thiazolidinediones and diabetic nephropathy-relevance to renoprotection", Nat. Clin. Pracice Nephrology vol. 1, No. 1 pp. 33-43 (2005).

Pautot et al., "Production of Unilamellar Vesicles Using an Inverted Emulsion", Langmuir 19, pp. 2870-2879 (2003).

Stallone et al., "Rapamycin for Treatment of Chronic Allograft Nephropathy in Renal Transplant Patients", J. of Am. Soc. of Nephrology, 16, pp. 3755-3762 (2005).

Tillier et al., "Determination of halofuginone in poultry feeds by high-performance liquid chromatography", J. of Chromatograpy 441, pp. 406-416 (1988).

Tumlin et al., "A Prospective, Open-Label Trial of Sirolimus in the Treatmen of Focal Segmental Glomerulosclerosis", Clin. J. Am. Soc. Nephtol. 1, pp. 109-116 (2006).

Vignot et al., "mTOR-targeted therapy of cancer with rapamycin derivatives", Annuals of Oncology 16: pp. 525-537 (2005).

Xu et al., "Pharmacogenomic profiling of the P13K/PTEN-AKT-mTOR pathway in common human tumors", Int. J. of Oncology 24, pp. 893-900 (2004).

\* cited by examiner

EMBOLIC DELIVERY OF THERAPEUTIC AGENTS

FIELD

This invention relates to the fields of organic chemistry, polymer chemistry, material science, pharmacology, physiology and medicine. In particular it relates to a method for the embolic delivery of therapeutic agents.

BACKGROUND

Therapeutic agents may be administered either systemically or locally. Systemic delivery involves the administration of a therapeutic agent at a discrete location followed by the dispersal of the agent throughout the patient's body including, of course, to the target treatment site or organ. In order to achieve a therapeutically effective amount of the agent at the afflicted site, it is usually necessary to administer an initial dose substantially greater than the therapeutically effective amount to account for the dilution the agent undergoes as it travels through the body. Systemic delivery is carried out primarily in two ways: introduction of the therapeutic agent into the digestive tract (enteral administration) or into the vascular system (parenteral administration), either directly such as injection into a vein or an artery or indirectly such as injection into a muscle or into the bone marrow. Delivery by each of these routes is strongly influenced by the so-called ADMET factors: absorption, distribution, metabolism, excretion and toxicity. For enteric administration, such factors as a compound's solubility, its stability in the acidic environs of the stomach and its ability to permeate the intestinal wall all affect the extent to which the drug is absorbed and therefore its bioavailability. For parenteral delivery factors such as enzymatic degradation, the lipophilic/hydrophilic partitioning coefficient, protein binding, etc. will affect the bioavailability of an agent.

Local delivery comprises administration of the therapeutic agent directly to the target site. The ADMET factors tend to be less important than with systemic administration since the agent is being administered essentially directly to the treatment site. Thus, the initial dose can be at or very close to the therapeutically effective amount. This permits a more economic use of therapeutic agent. Further, since administration is local, a lower therapeutic index can be tolerated without adverse side effects. In fact, the benefits of local delivery over systemic delivery militate in favor of the former if the disease being treated is localized to a specific organ or tissue.

A current means of local delivery of therapeutic agents for the treatment of vascular disease is use of a drug-eluting stent (DES). A stent is coated with a drug-containing polymer, inserted into a patient's vessel, advanced to the diseased locale and deposited there. The drug then elutes from the stent and performs its therapeutic function. This approach is appropriate for diseased tissues that are accessible to fairly large, physiologically speaking, stents. Many tissue locales, however, are not so conveniently located and the afflicted region may be well away from the nearest vessel amenable to stenting. Thus, while the use of a drug-coated stent would still bring the therapeutic agent closer to the afflicted area than could be achieved by systemic delivery, delivery of the therapeutic agent would still depend on passive diffusion to reach the diseased tissue.

What would be beneficial is a method of getting substantially closer to the diseased regions of a tissue and to be able to control to some extent the diffusion of the drug in the diseased tissue. The current invention provides such a method.

SUMMARY

Thus, in one aspect the current invention relates to a method of treating a diseased tissue, comprising:
providing a therapeutic agent that is known or found to be active against a causal factor of the disease;
combining the therapeutic agent with a biocompatible carrier;
forming the therapeutic agent/carrier combination into a plurality of microparticles wherein the microparticles have a narrow size distribution with a mean size that will result in at least 80% of the microparticles being entrapped by the circulatory capillary system at a selected point of treatment on a first pass; and,
administering the microparticles to a patient in need thereof through an artery that directly serves the diseased tissue.

In an aspect of this invention, at least 90% of the microparticles are entrapped on the first pass.

In an aspect of this invention, at least 99% of the microparticles are entrapped on the first pass.

In an aspect of this invention, if more than one therapeutic agent is used, each therapeutic agent is separately formed into a plurality of microparticles with a separate carrier wherein the carrier may be the same or different for each therapeutic agent.

In an aspect of this invention, if more than one therapeutic agent is used, the therapeutic agents are combined with one carrier and formed into the plurality of microparticles.

In an aspect of this invention, the therapeutic agent or therapeutic agents is/are combined with a carrier at different therapeutic agent concentrations, each concentration/carrier combination being separately formed into a plurality of microparticles.

In an aspect of this invention, two or more therapeutic agents are combined with a single carrier, with separate populations of the same carrier or with different carriers at independently selected therapeutic agent concentrations, each concentration/carrier combination being separately formed into a plurality of microparticles.

In an aspect of this invention, the mean particle size is about 8 microns to about 20 microns.

In an aspect of this invention, the mean particle size is from about 10 to about 15 microns.

In an aspect of this invention, the mean particle size is about 12.5 to about 13.5 microns.

In an aspect of this invention, the microparticles are substantially spherical and the mean size is a mean diameter.

In an aspect of this invention, the narrow size distribution is obtained by emulsification followed by supercritical fluid solvent extraction.

In an aspect of this invention, the narrow size distribution is obtained by ultrasonic spraying.

In an aspect of this invention, the narrow size distribution is obtained by acoustic excitation of a liquid stream into droplets that are subsequently hardened.

In an aspect of this invention, the narrow size distribution is obtained by emulsification, suspension or precipitration polymerization.

In an aspect of this invention, the narrow size distribution is obtained by electrohydrodynamic atomization, membrane emulsification, ultrasonic atomization or piezoelectric atomization.

In an aspect of this invention, the diseased tissue is selected from the group consisting of kidney, liver, lung, heart, brain, spleen, prostate, ovary, organ post-transplant rejection and malignant neoplastic tissue.

In an aspect of this invention, the kidney tissue disease is selected from the group consisting of chronic kidney disease, diabetic nephropathy, focal segmental glomerulosclerosis, IgA nephritis, lupus nephritis, reflux nephropathy, glomerulonephritis, glumerulonephrosis and polycystic renal disease.

In an aspect of this invention, the therapeutic agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF and combinations thereof.

In an aspect of this invention, the TGF-β pathway inhibitor is halofuginone.

In an aspect of this invention, the halofuginone piperidine nitrogen comprises an ammonium salt with a hydrophobic counterion.

In an aspect of this invention, the hydrophobic counterion is selected from the group consisting of acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, ε-hydroxycaproate, 3-hydroxybutylrate, 4-hydroxybutyrate, 3-hydroxyvalerate, an anion of a fatty acid, an anion of an organic phosphate and an anion of an organic sulfate.

In an aspect of this invention, the protein kinase C pathway inhibitor is ruboxistaurin.

In an aspect of this invention, the mTOR inhibitor is selected from the group consisting of sirolimus, everolimus, zotarolimus, pimecrolimus, temsirolimus and biolimus.

In an aspect of this invention, the biocompatible carrier is biodegradable.

In an aspect of this invention, the biodegradable carrier comprises a biodegradable polymer.

In an aspect of this invention, the biodegradable polymer is poly(lactide-co-glycolide).

In an aspect of this invention, the lactide is selected from the group consisting of 1-lactide, d/l-lactide and meso-lactide.

In an aspect of this invention, the biodegradable polymer degrades under physiological conditions such that a therapeutic concentration of the therapeutic agent is released over about 1 hour to about a week.

In an aspect of this invention, the biodegradable polymer degrades under physiological conditions such that a therapeutic concentration of the therapeutic agent is released over about 1 week to about 4 weeks.

In an aspect of this invention, the biodegradable polymer degrade under physiological conditions such that a therapeutic concentration of the therapeutic agent is released over about 1 month to about 12 months.

DETAILED DESCRIPTION

It is understood that use of the singular throughout this application including the claims includes the plural and visa versa unless expressly stated otherwise. That is, "a" and "the" are to be construed as referring to one or more of whatever the word modifies. Non-limiting examples are: "a therapeutic agent" which is understood to include one such agent, two such agents or, under the right circumstances, as determined by those skilled in the treatment of diseased tissues, even more such agents unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, "substantial" or "substantially" means that the object of the adjective or adverb is not a perfect example of such object but would be immediately envisaged by the skilled artisan to warrant the general designation. That is, when modified by the word "substantially," it is understood that the object of the modifier would be considered close enough to be recognized by those of ordinary skill in the art as being within the general genus of such objects. As a non-limiting example relating to the current invention, "substantially spherical" refers to an object that, while not a mathematically perfect sphere, would be easily recognized as being within reasonable bounds of that which those skilled in the art would readily consider generally "spherical."

The use of other words or approximation herein, such as "about" or "approximately" when used to describe numerical values or ranges likewise are understood to mean that those skilled in the art would readily consider a value different from the exact number or outside the actual range to be close enough to be within the aegis of that number or range. At the very least, "about" or approximately is understood to mean±15% of a given numerical value or range starting and ending point.

As used herein, "treating" refers to the administration of a therapeutically effective amount of a therapeutic agent to a patient afflicted with a diseased tissue.

A "patient" refers to any species that might benefit from treatment using the method herein but at present is preferably a mammal and most preferably a human being.

As used herein, a "tissue," while generally referring to any group of cells that in the aggregate perform the same function, refers specifically to tissues that receive blood through a dedicated arterial system, such tissues including, without limitation, the lungs (pulmonary artery), liver (hepatic artery), kidneys (renal artery) and heart (coronary artery).

As used herein, a "diseased tissue" refers to a tissue in which there is a disturbance of normal functioning due to a pathological condition characterized by recognizable symptoms and signs.

As used herein, a "therapeutic agent" refers to any substance that, when administered in a therapeutically effective amount to a patient, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease.

Examples of therapeutic agents that may be suitable for use in the method of this invention depending, of course, on the specific disease being treated, include, without limitation, anti-restenosis, pro- or anti-proliferative, anti-inflammatory, anti-neoplastic, antimitotic, anti-platelet, anticoagulant, anti-fibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective agents.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, everolimus, Biolimus A9 (Biosensors International, Singapore), deforolimus, AP23572 (Ariad Pharmaceuticals) and perfenidone.

Examples of anti-inflammatory agents include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin agents include, without limitation, heparin, sodium heparin, low molecular weight heparins, heparinoids, hirudin, bivalirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiogensin II receptor antagonists include, without limitation, irbesartan and losartan.

Other therapeutic agents that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy, antiviral agents and diuretics.

Presently preferred therapeutic agents are halofuginone, ruboxistaurin, sirolimus, everolimus, zotarolimus, temsirolimus, pimecrolimus and biolimus. In particular, but without limitation, these agents are useful for the treatment of renal diseases.

A "therapeutically effective amount" refers to that amount of a therapeutic agent that will have a beneficial effect, which may be curative or palliative, on the health and well-being of the patient so afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period of about an hour to about 3 days. Medium-term sustained release refers to administration of a therapeutically effective amount of a therapeutic agent over a period of about 3 days to about 4 weeks and long-term refers to the delivery of a therapeutically effective amount over any period in excess of about 4 weeks, but in particular at present about 4 weeks to about a year.

As used herein, a "causal factor" refers to an abnormal biochemical process that at last in part results in the particular tissue disease as manifested by symptoms and signs that characterize the disease.

As used herein, an "artery that directly services the diseased tissue" refers to an artery sufficiently near the diseased tissue that blood entering that artery must proceed by means of the circulatory system into and through the diseased tissue such that the microparticles of this invention are entrapped entirely or at least predominantly in the target diseased tissue. Such arteries include, without limitation, the coronary artery, the bronchial artery, the hepatic artery and the renal artery.

As used herein, "combining" a therapeutic agent with a biocompatible carrier refers simply to the physical mixing of the agent and the carrier to form a substantially homogeneous mixture.

As used herein a "carrier" refers to the substance that constitutes the continuous phase of a microparticle, if solid, or the contents of the core if core-shell in structure.

As used herein, "biocompatible" refers to a property of a material characterized by it, or its physiological degradation products, being not, or at least minimally, toxic to living tissue; not, or at least minimally and reparably, otherwise injurious living tissue; and/or not, or at least minimally and controllably, causative of an immunological reaction in living tissue. With regard to salts, both the cation and anion must be biocompatible.

As used herein, a "counterion" refers to an ion of opposite charge to another ion in a salt such that electronic neutrality is maintained. For example, sodium ($Na^+$) is the counterion of chloride ($Cr$) in common table salt, NaCl, and visa versa.

Examples of generally biocompatible cations include, without limitation, sodium ($Na^+$), potassium ($K^+$), calcium ($Ca^+$), magnesium ($Mg^{++}$), iron ($Fe^{++}$), ammonium ($NH_4^+$) and organic ammoniums formed by protonation of a amine nitrogen of a therapeutic agent. Others are well-known to those skilled in the art and are within the scope of this invention.

A presently preferred cation is that arising from the protonation of the piperidine nitrogen of halofuginone:

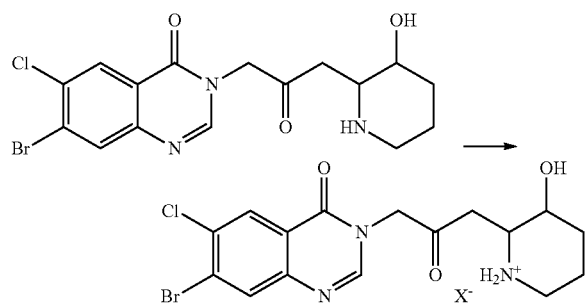

It is presently preferred that anionic counterions to the above cations such as, without limitation, $X^-$ above, be hydrophobic. One of the advantages of using such anions is that the resulting salt may be solvent soluble, a desirable characteristic for the formation of microparticles of this invention. Examples of generally biocompatible hydrophobic anions include, without limitation, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, $\epsilon$-hydroxycaproate, 3-hydroxybutylrate, 4-hydroxybutyrate, 3-hydroxyvalerate, anions of fatty acids, anion of organic phosphates and anions of organic sulfates.

As used herein, "forming the therapeutic agent/carrier combination into a plurality of microparticles" means to subject the combination to whatever protocol is required to convert the simple mixture of the agent and carrier into the desired structural vehicle for delivery of the therapeutic agent to the diseased tissue.

Structural vehicles that may be used with the method of this invention include, without limitation, liposomes, polymersomes and solid microparticles of a mean size such that at least 80% of them will not be able to traverse the capillary system of a patient, in particular a human being. To accomplish this, it is present preferred that the microparticles have a mean size that is in the range or about 10 microns to about 15 microns, more preferably at present about 12.5 to about 13.5 microns.

Particle size distributions may be represented in a number of ways, one of the most common of which is "mean size." A "mean" size may refer to a value based on particle length, width and/or diameter, on area or on volume. As used herein, "mean size" is determined by measuring the longest through-particle distance of each microparticle and then dividing by the total number of microparticles. Of course, this requires sophisticated equipment when dealing with the large numbers of microparticles contemplated by this invention but such equipment is well-known and readily available to those skilled in the art and such determination of mean size is commonplace in the art. To assure efficient capture of the microparticles of this invention at the capillary bed, not only should the microparticles have the stated mean size, the distribution of particle size should be a narrow as possible, that is as close to monodisperse as can be achieved. No specific size distribution is presently preferred because the narrower the better and, while several techniques are discussed below for achieving relatively narrow size distributions, as technology advances, equipment and procedures for reaching even narrower size distributions will surely become available and all such equipment, procedures and size distributions will clearly be within the scope of this invention.

With regard to mean size and size distribution, as noted above, it is presently preferred that at least 80% of the microparticles administered into an artery serving a particular tissue are entrapped in the capillary system at the terminus of that artery. More preferably, at least 90% of the microparticles will be entrapped and most preferably at present, at least 99% of the microparticles will be entrapped.

The plurality of microparticles herein can comprise several different designs. In the simplest, the therapeutic agent is simply encapsulated in the carrier at a single concentration so that all microparticles are substantially the same with regard to drug load. In another design, the therapeutic agent can be encapsulated in the carrier, or if desired in different carriers, at different concentrations in separate preparations and the microparticles formed in those separate preparations can be combined for administration to a patient. In yet another design, different therapeutic agents can be separately encapsulated in the carrier, or, again, if desired in different carriers, at various concentrations, the microparticles again being combined for administration. Two or more therapeutic agents can, of course, be encapsulated in the same carrier such that the resulting microparticles each contain more than one therapeutic agent. Those skilled in the art will, based on the disclosure herein, be able to devise additional combinations of carrier and therapeutic agent(s); all such combinations are within the scope of this invention.

The selection of the presently preferred range of particle sizes is based on the average diameter of capillaries in the human body. A basic premise of this invention is that microparticles containing an appropriate therapeutic agent or combination of agents can be administered into an artery that directly services a tissue of interest. By "directly services" is meant that blood flowing through the artery proceeds in one direction only through the labyrinthine maze comprising artery→arterioles→metarterioles→capillaries→postcapillary venules→venules-vein. It is noted that the kidneys have a rather unique circulatory system: arteries→afferent arterioles→glomerular capillaries→efferent arterioles but the methods of this invention are eminently suitable for use with the kidneys as well as other organs. Thus, microparticles injected into blood in the artery have nowhere to go but into the diseased tissue where, depending on their size, they lodge in whichever substructure in the preceding chain has a diameter that is smaller than the selected particle mean size (or mean diameter in the case of substantially spherical microparticles). In this light it is noted that arterioles are generally regarded as having interior diameters in the range of approximately 10 to 50 microns, metarterioles about 10 to 20 microns and capillaries approximately 4 to 15 (average about 8) microns in diameter. Thus, microparticles having a mean size of about 10 to 15 micrometers should be efficiently entrapped once they reach the capillaries. In fact, it has been reported that in one experiment 97% of 15 micrometer radiolabeled microspheres reaching the eye were entrapped at the first pass.

Entrapping the microparticles at the capillary level assures that the target diseased tissue receives the maximum benefit of the therapeutic agent encapsulated in the microparticles. This is due to the physiology of the capillary system. That is, the capillary system comprises a vast network of minute (averaging approximately 1 millimeter in length and 8 microns in diameter) vessels that permeates virtually every tissue in the mammalian body. As testament to the ubiquity of capillaries, it has been estimated that their number is approximately 19,000,000,000 and that most living tissue cells lie within 1-3 cell lengths of a capillary. Thus, to achieve maximum deployment of a therapeutic agent in a target tissue, it makes sense that the vehicle carrying the therapeutic agent be capable of maneuvering through the circulatory system to the capillary level. Administering the microspheres at the level of the arteriole or capillary also minimizes any potential embolic effect. As most cells lie within 1-3 cell lengths of multiple capillaries, when one capillary is embolized any ischemia created is confined to a very small zone of tissue. Cells in this zone can also received oxygen and nutrients from adjacent capillaries, which further prevents or minimizes ischemia. If larger microspheres are used, for example particles with a mean size greater than 20 microns, the zone of tissue embolized becomes proportionately greater. If cells at or near the center of this larger embolized region cannot be sufficiently perfused then frank necrosis may result.

As used herein, a "microparticle" refers to a solid having as its smallest cross-sectional, i.e., through the solid as opposed to along its surface, dimension about one micron. Presently preferred are microparticles having a mean size of about 10 to about 15 microns, still more preferably at present about 12.5 to about 13.5 microns. The solid can have any desired shape such as without limitation spherical, ellipsoid, rod-like, entirely random shaped, etc., although substantially spherical microparticles are well-known in the art, are readily prepared and are presently preferred. The microparticle may be constructed of one or more biocompatible substances and may be porous so as to permit elution of the therapeutic substance embedded in it or may be biodegradable such that as the particle degrades the therapeutic substance is released into the environment.

As used herein, a "liposome" refers to a core-shell structure in which the shell comprises phospholipids or sphigolipids that surround a usually liquid, and in most cases aqueous, core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

Liposomes may, for example without limitation, be immuno-targetted for use in treating diabetic nephropathy. The technique is similar to that disclosed in Ishida, et al., "A combinatorial approach to producing sterically stabilized (Stealth) immunoliposomal drugs," *FEBS Letters*, 1999, 460:

1290133. In brief, the method involves loading liposomes with halofuginone or another TGF-6 pathway inhibitor by rehydration or reverse evaporation and subsequent extrusion or using some other standard technique well-known in the art. In a separate step, a targeting moiety such as, without limitation, an OX7 fab-fragment is conjugated to another lipid; e.g., the OX7 can be conjugated to maleimide-terminated poly (ethylene glycol) covalently linked to distearoylphosphatidyl-ethanolamine. Then the halofuginone-loaded liposomes are co-incubated with the lipid-conjugated targeting moiety such that the lipid-anchored targeting molecules insert into the membrane of the liposome. The result is a kidney-targeted liposome.

In addition to solid microparticles and liposomes, a particle of this invention may be a polymersome, which is akin to a liposome wherein the shell is made up of synthetic amphiphilic polymers rather than phospholipids and sphigolipids. Examples of polymers that can be used to prepare polymersomes include, without limitation, poly(ethylene glycol)-b-poly($\epsilon$-caprolactone), poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates). Depending on the length and chemical nature of the polymers in the diblock copolymer, polymersomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate therapeutic agents by including the therapeutic agent in the water used to rehydrate the copolymer film. Polymersomes can also be force-loaded by osmotically driving the therapeutic agent into the core of the vesicle. Also as with liposomes, the loading efficiency is generally low. Recently, however, a technique has been reported that provides polymersomes of relative monodispersity and high loading efficiency; generation of polymersomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation. This technique along with any other technique know in the art or as may become known in the future can be used to prepare a composition of therapeutic agents for use in or on a delivery interface of this invention.

As mentioned previously, presently preferred are microparticles, liposomes and polymersomes having a mean particle size of about 10 to about 15 micrometers, even more preferably at present about 12.5 to 13.5 micrometers.

As used herein, "first pass" refers to the first time a particle encounters the capillary bed at the terminus of a selected artery serving a diseased tissue. Microparticles that, for one reason or another, pass through the bed and find their way to venules and thence to veins will continue to circulate in the circulatory system until they once again encounter a capillary bed (although it may not be the capillary bed of the target tissue, which is why it is preferred that as high a percentage as possible are entrapped in the capillary bed of the target diseased tissue after having been administered into an artery serving that tissue). Again, for the purpose of this invention, it is preferred that at least 80% of the microparticles are entrapped at the first pass, more preferably 90% and presently most preferably, 99%.

As mentioned above, in order to achieve the preceding degrees of entrapment it is necessary to produce microparticles having a size distribution a narrow as possible around the target mean size wherein the target mean size is determined by the vessel size in the tissue being treated. That is, the mean particle size must be small enough to pass through an afferent arteriole (in the case where a kidney is the target tissue) but large enough to be trapped by a capillary. While there may be other means to accomplish this and any such means is within the scope of this invention, presently preferred means include emulsification followed by supercritical fluid solvent extraction, ultrasonic atomization or droplet formation, electrohydrodynamic atomization and membrane emulsification.

Emulsification followed by supercritical fluid solvent extraction to form microparticles having a very narrow size range is a well-known technique in the art and therefore need not be extensively discussed herein, In brief, the technique involves the formation of an emulsion by dissolving a polymer and a therapeutic agent in a solvent for both, adding the solution under high shear to water containing emulsifying agent, sonicating to achieve a narrow droplet size range, passing the droplets through a porous membrane of well-defined pore size and then extracting the solvent from the microparticles using a supercritical fluid to give a hardened particle. A supercritical fluid, that is a fluid above its critical temperature and pressure, is used because of the physical properties of such fluids, which are intermediate between those of a gas those of a liquid. For example, supercritical carbon dioxide has a viscosity in the range of about 0.02 to about 0.1 centipoise (cP) whereas liquids have viscosities 0.5-1.0 cP and gasses have viscosities around 0.01 cP. Further, the diffusivities of solutes in supercritical carbon dioxide are up to a factor of 10 higher than in liquid solvents. This and the tunability of the solvating properties of supercritical fluids, which are a complex (but relatively well-understood) function of pressure and temperature, permit extremely selective extraction of one material, the solvent herein for instance, from others it may be combined with.

In any event, the hardened microparticles obtained after supercritical fluid solvent extraction may then be passed through yet another filter with well-defined pore size to still further control particle size distribution.

Atomization of a solution using an ultrasonic transducer can produce relatively monodisperse droplets. When captured in a appropriate bath and hardened, this can result in a narrow distribution of microspheres. The ultrasonic energy may be applied using a "horn" with the solution either flowing through it or being applied to its surface. The ultrasonic horn oscillates at a fixed frequency supplied by an ultrasonic transducer. Ultrasonic spray nozzles of this sort are readily available from Sono-Tek Corp, Milton, N.Y.

Another technique that produces relatively monodisperse particles involves the use of acoustic excitation of a liquid stream to break the stream up into monodisperse particles (Berkland, et al., J. Control. Rel., 2001, 73:59-74). The liquid stream is composed of a polymer and a therapeutic agent dissolved in one or more solvents. The droplets are carried by a carrier stream to a hardening bath where the solvent is removed. The frequencies needed to excite the liquid stream sufficiently to break it up into droplets are in the ultrasonic region of the spectrum.

Electrohydrodynamic atomization (EDHA) is another, relatively new but nevertheless well-characterized technique in the art for producing narrow size distribution, i.e. essentially monodisperse, microparticles. Again, without going into unnecessary detail since those skilled in the art will be very familiar with the technique, electrohydrodynamic atomization involves pumping a solution through a nozzle wherein a high voltage potential has been established between the tip of the nozzle and a counter-electrode. The high potential causes a build-up of electric charge in droplets at the nozzle tip and when the coulombic forces exceed the surface tension of the droplets, they separate, essentially explode, into smaller droplets. If parameters are optimized to achieve a stable spray, monodispersed droplets are obtained. Removal of solvent from the droplets yields monodisperse solid microparticles. Parameters that may be varied to achieve a particular average size droplet/particle include, without limitation, the applied voltage, the flow rate, density, conductivity and surface tension.

Normal emulsification techniques generally afford droplets of relative polydispersity, at least with regard to the narrow size distribution desired for use in the current invention. Thus, the requirement of one and perhaps two filtrations as set forth above with regard to emulsification/supercritical fluid solvent extraction. This is due primarily to the myriad parameters that come into play when preparing an emulsion such as, without limitation, the concentration of the agents, the nature of the drug/polymer/surfactant/solvent interaction, polymer molecular weight, sonication power, stir speed, fluid dynamics of the system and temperature. These shortcomings, at least with regard to the present invention, can be overcome by using the technique known as membrane emulsification.

Membrane emulsification is another relatively new technique for producing essentially monodisperse microparticles. As with standard emulsification followed by multiple filtrations and electrohydrodynamic atomization, membrane emulsification, while a relatively recent development, is well-known to those skilled in the art and need not be detailed herein. In brief, membrane emulsification involves the injection of an intended discontinuous phase through a porous membrane in which pore size is very carefully controlled into the intended continuous phase, which is moving past the porous membrane on the side opposite that from which the discontinuous phase is being injected. Droplets are sheared off the membrane by the moving continuous phase. Control of droplet size is quite exquisite compared to normal emulsification techniques because size is determined predominantly by easily varied parameters including the speed of the continuous phase, viscosity of the continuous phase, interfacial tension between the phases, the chemistry of the system—surfactant type and physical properties of all the constituents—and, of course, pore size. Newer techniques for creating porous membranes with a very precise pore size such as laser drilling and lithographic procedures have made membrane emulsification even more attractive as a technique for control of particle size distribution.

Polymers are presently preferred carriers for use in the preparation of microparticles of the present invention. The polymers must be biocompatible and can be either biostable or biodegradable. As used herein, biodegradable includes all means by which a polymer can be disposed of in a patient's body, which includes bioabsorption, resorption, etc. Biostable simply means that the polymer does not biodegrade or bioabsorb under physiological conditions over a relatively long period of time that may reach years.

Physiological conditions merely refers to the physical, chemical and biochemical milieu that constitutes the mammalian body and includes, without limitation, pH, temperature, enzymes and the presence of destructive cells such as phagocytes.

Among biocompatible, relatively biostable polymers useful as carriers for the preparation of microparticles of this invention are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers that can be used for the carrier/particle-forming of this invention include, again without limitation, naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Synthetic or semi-synthetic biocompatible, biodegradable polymers may also be used as carriers for the purpose of this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyester urethanes, polyester urethane ureas, polyhydroxyacids, polyhydroxyalkanoates, polyanhydrides, polyesters, polyorthoesters, polyamino acids, polyoxymethylenes, poly (ester amides) and polyimides.

Further non-limiting examples of biocompatible biodegradable polymers that may be suitable as carriers herein include, without limitation, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly (trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly (α-hydroxyacids), poly(β-hydroxyacid) such as poly(3-hydroxybutyrate) (PHB), poly(3-hydroxybutyrate-co-valerate) (PHBV), poly(3-hydroxyprorionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

A presently preferred polymer for use as a carrier/particle former is poly(lactide-co-glycolide), a random copolymer comprising a lactide to glycolide weight/weight ratio of about 90:10 to about 50:50, preferably at present, 75:25 and most preferably at present 85:15.

As noted previously, the method of this invention can be used to treat any diseased tissue to which blood is supplied by a dedicated, relatively reachable artery such as the renal, hepatic, pulmonary and cardiac arteries. A presently preferred diseased tissue to be so treated, however, is kidney tissue disease such as, without limitation, chronic kidney disease, diabetic nephropathy, focal segmental glomerulosclerosis, IgA nephritis, lupus nephritis, reflux nephropathy, glomerulonephritis, glomerulonephrosis and polycystic renal disease. Further, treatment of particular biochemical pathways, abnormal functioning of which are associated with these diseases, is also presently preferred. Among these are halofuginone, ruboxistaurin and the 'olimus drugs.

Nephropathy is one of the most common microvascular complications associated with diabetes and is currently the leading cause of end-stage renal disease. Of the numerous causal factors associated with diabetic nephropathy, dislipidemia, hypertension, hyperglycemia and activation of the renin-angiotensin system all have been linked to a common intracellular signaling pathway, the activation of protein kinase C β (PKC β). Activation of PKC β appears to result in reduced availability of nitric oxide in endothelial cells leading to impaired endothelial-dependent vasodilation. Inhibiting PKC β has implicated in the reduction of albuminuria and messangial expansion, both of which are associated with kidney malfunction and nephropathy. Thus, an inhibitor of PKC β would be expected to have a beneficial therapeutic effect. Ruboxistaurin:

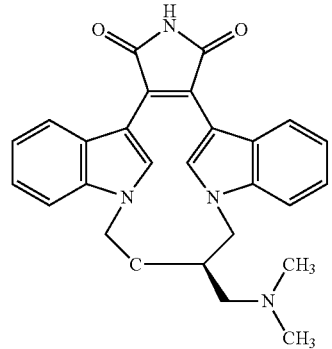 [SMILES: CN(C)C[C@H]1CCn2cc(c3ccccc32)C2=C(C(=O)NC2=O)c2cn(c3ccccc23)C1]

has been shown to be an effective inhibitor of PKC β and therefore is a currently preferred therapeutic agent of this invention for treating diabetic nephropathy.

Halofuginone, described above, is likewise presently particularly preferred for the treatment of diabetic nephropathy because it is a transforming growth factor beta (TGF-β) inhibitor and TGF-β has also been implicated as a key participant in the cascade of events culminating in diabetic nephropathy. That is, TGF-β has been shown to promote renal cell hypertrophy and to regulate the production of extra-cellular matrix molecules while its inhibition appears to prevent the hypertrophic effects of high glucose and the stimulation of matrix synthesis in renal cells. Thus, halofuginone is expected to have a marked salutary effect on this kidney disease.

Another presently preferred therapeutic agent for the treatment of diabetic nephropathy is rapamycin and its derivatives and analogs, which includes, without limitation sirolimus (rapamycin itself), everolimus, zotarolimus, temsirolimus, and biolimus. The Akt/mammalian target of rapamycin (mTOR) pathway has been implicated in the development and progress of diabetic nephropathy. mTOR inhibition by rapamycin has been shown to reduce, glomular enlargement, albuminuria, glomular basement membrane thickening, renal macrophage recruitment and levels of mRNA expression of proliferating cell nuclear antigen and TGF β, as well as other diabetic nephropathy causal factors and thus would be expected to have a substantial salutary effect in the treatment of diabetic nephropathy.

EXAMPLES

Example 1

The membrane emulsification technique was examined. A mixture of poly(lactide-co-glycolide) (85:15), everolimus and dichloromethane was driven through a Nanomi® membrane system into water. The solvent was removed by evaporation and the water was removed by lyophilization. The resultant microparticles had a median diameter of about 12 microns and a very narrow polydispersity. The microparticles had a drug loading of 42% by weight. Their in vitro release rate was similar to that obtained when the microparticles were prepared using standard emulsification techniques.

Example 2

There are approximately 30,000 glomeruli in a rat kidney. Polystyrene microparticles having a mean size in the range of 10-15 microns were injected into the rat renal artery and the kidneys harvested 4 or 8 weeks later. In all rats, microparticles were found exclusively in the capillaries of the glomeruli. Only when in excess of 500,000 microparticles were injected (approximately 16 microparticles per glomerulus) were microparticles found anywhere but in the glomeruli capillaries. Minimal adverse biological response to the microparticles at either 4 or 8 weeks was observed. Likewise, no adverse vascular events related to microparticle injection were evident at 4 or 8 weeks (e.g., no microparticle clumping was observed).

It is understood that while various aspects of this invention are described above in the context of specific embodiments, examples, materials, equipment procedures and techniques, those skilled in the art will find additional means, materials, equipment, procedures and techniques based on the disclosures herein to accomplish the same end. All such means, procedure and techniques are within the scope of this invention.

What is claimed:

1. A method of treating a diseased tissue, comprising:
   providing a therapeutic agent that is known or found to be active against a causal factor of the disease;
   combining the therapeutic agent with a biocompatible carrier;
   forming the therapeutic agent/carrier combination into a plurality of microparticles wherein the microparticles have a narrow size distribution with a mean size of about 10-15 microns such that at least 80% of the microparticles are entrapped by the circulatory capillary system at a selected point of treatment on a first pass; and,
   administering the microparticles to a patient in need thereof through an artery that directly serves the diseased tissue.

2. The method of claim 1, wherein at least 90% of the microparticles are entrapped on the first pass.

3. The method of claim 1, wherein at least 99% of the microparticles are entrapped on the first pass.

4. The method of claim 1, wherein if more than one therapeutic agent is used, each therapeutic agent is separately formed into a plurality of microparticles with a separate carrier wherein the carrier may be the same or different for each therapeutic agent.

5. The method of claim 1, wherein if more than one therapeutic agent is used, the therapeutic agents are combined with one carrier and formed into the plurality of microparticles.

6. The method of claim 1, wherein the therapeutic agent or therapeutic agents is/are combined with a carrier at different therapeutic agent concentrations, each concentration/carrier combination being separately formed into a plurality of microparticles.

7. The method of claim 1, wherein two or more therapeutic agents are combined with a single carrier, with separate populations of the same carrier or with different carriers at independently selected therapeutic agent concentrations, each concentration/carrier combination being separately formed into a plurality of microparticles.

8. The method of claim 1, wherein the mean particle size is about 12.5 to about 13.5 microns.

9. The method of claim 1, wherein the microparticles are substantially spherical and the mean size is a mean diameter.

10. The method of claim 1, wherein the narrow size distribution is obtained by emulsification followed by supercritical fluid solvent extraction.

11. The method of claim 1, wherein the narrow size distribution is obtained by ultrasonic spraying.

12. The method of claim 1, wherein the narrow size distribution is obtained by acoustic excitation of a liquid stream into droplets that are subsequently hardened.

13. The method of claim 1, wherein the narrow size distribution is obtained by emulsification, suspension or precipitation polymerization.

14. The method of claim 1, wherein the narrow size distribution is obtained by electrohydrodynamic atomization, membrane emulsification, ultrasonic atomization or piezoelectric atomization.

15. The method of claim 1, wherein the diseased tissue is selected from the group consisting of kidney, liver, lung, heart, brain, spleen, prostate, ovary, organ post-transplant rejection and malignant neoplastic tissue.

16. The method of claim 15, wherein the kidney tissue disease is selected from the group consisting of chronic kidney disease, diabetic nephropathy, focal segmental glomerulosclerosis, IgA nephritis, lupus nephritis, reflux nephropathy, glomerulonephritis, glumerulonephrosis and polycystic renal disease.

17. The method of claim 16, wherein the therapeutic agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF and combinations thereof.

18. The method of claim 17, wherein the TGF-β pathway inhibitor is halofuginone.

19. The method of claim 18, wherein the halofuginone piperidine nitrogen comprises an ammonium salt with a hydrophobic counterion.

20. The method of claim 19, wherein the hydrophobic counterion is selected from the group consisting of acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, c-hydroxycaproate, 3-hydroxybutylrate, 4-hydroxybutyrate, 3-hydroxyvalerate, an anion of a fatty acid, an anion of an organic phosphate and an anion of an organic sulfate.

21. The method of claim 17, wherein the protein kinase C pathway inhibitor is ruboxistaurin.

22. The method of claim 17, wherein the mTOR inhibitor is selected from the group consisting of sirolimus, everolimus, zotarolimus, pimecrolimus, temsirolimus and biolimus.

23. The method of claim 1, wherein the biocompatible carrier is biodegradable.

24. The method of claim 23, wherein the biodegradable carrier comprises a biodegradable polymer.

25. The method of claim 24, wherein the biodegradable polymer is poly(lactide-co-glycolide).

26. The method of claim 25, wherein the lactide is selected from the group consisting of l-lactide, d,l-lactide and meso-lactide.

27. The method of claim 24, wherein the biodegradable polymer degrades under physiological conditions such that a therapeutic concentration of the therapeutic agent is released over about 1 hour to about a week.

28. The method of claim 24, wherein the biodegradable polymer degrades under physiological conditions such that a therapeutic concentration of the therapeutic agent is released over about 1 week to about 4 weeks.

29. The method of claim 24, wherein the biodegradable polymer degrade under physiological conditions such that a therapeutic concentration of the therapeutic agent is released over about 1 month to about 12 months.

* * * * *